Figure 1:
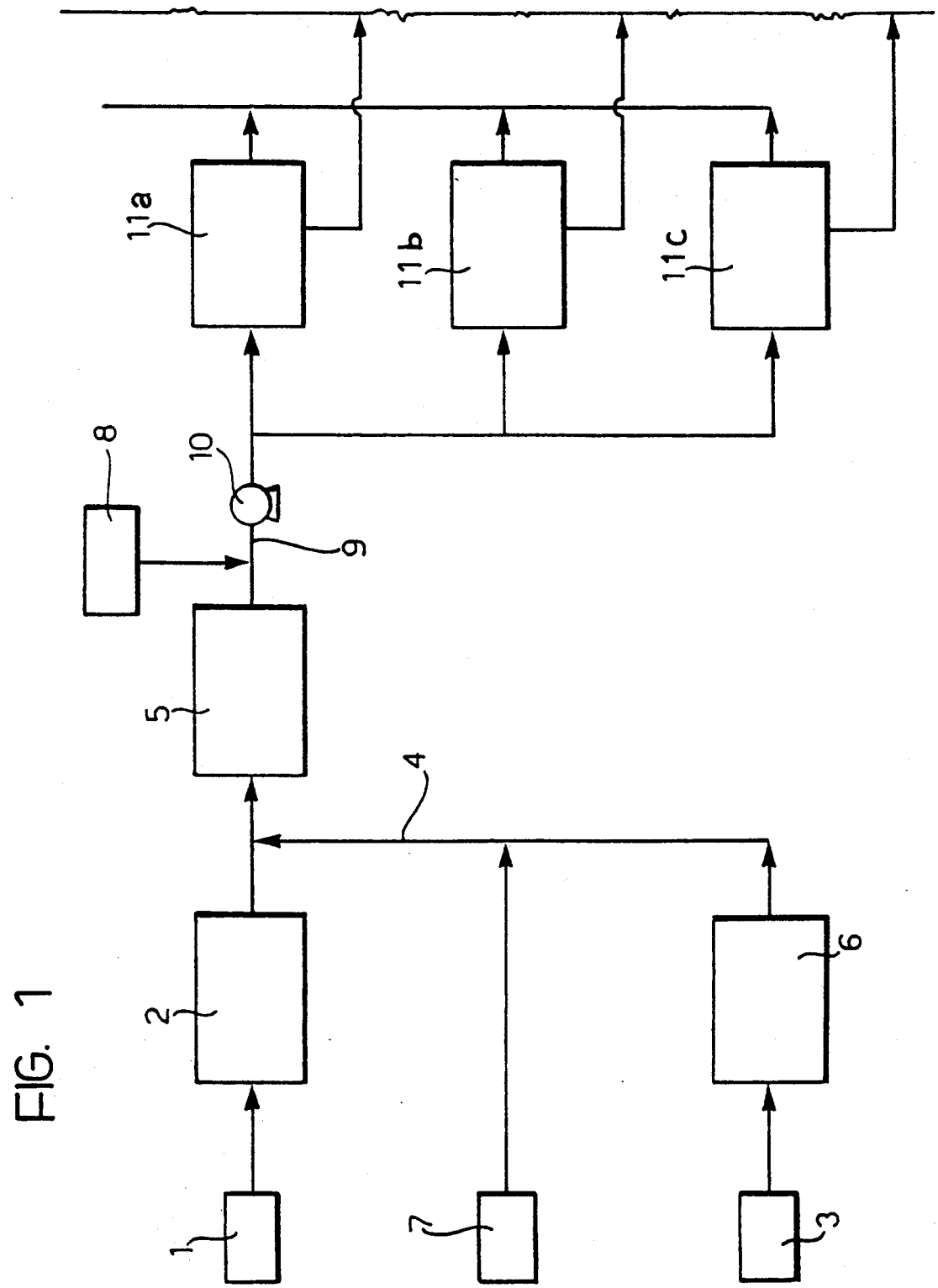

United States Patent [19]

Pellegrin et al.

[11] Patent Number: 5,207,911

[45] Date of Patent: May 4, 1993

[54] METHOD FOR THE BREAKDOWN AND RECYCLING OF SOLID URBAN WASTE BY ANAEROBIC FERMENTATION

[75] Inventors: Roberto Pellegrin; Silvio Tasca; Franco Tasca, all of Turin, Italy

[73] Assignee: Rosewell Limited, Dublin, Ireland

[21] Appl. No.: 572,986

[22] PCT Filed: Mar. 2, 1989

[86] PCT No.: PCT/EP89/00212

§ 371 Date: Sep. 7, 1990

§ 102(e) Date: Sep. 7, 1990

[87] PCT Pub. No.: WO89/08616

PCT Pub. Date: Sep. 21, 1989

[30] Foreign Application Priority Data

Mar. 7, 1989 [IT] Italy .................. 67184 A/88

[51] Int. Cl.$^5$ .................................. C02F 3/28
[52] U.S. Cl. ........................ 210/603; 210/613; 210/622; 210/631
[58] Field of Search ............ 210/603, 605, 610-612, 210/613, 621-622, 631

[56] References Cited

U.S. PATENT DOCUMENTS

| | | | |
|---|---|---|---|
| 3,981,800 | 9/1976 | Ort ........................... | 210/603 |
| 4,067,801 | 1/1978 | Ishida et al. ............... | 210/631 |
| 4,323,367 | 4/1982 | Ghosh ........................ | 210/603 |
| 4,400,195 | 8/1983 | Rijkens ..................... | 210/603 |
| 4,684,468 | 8/1987 | De Baere .................... | 210/603 |

FOREIGN PATENT DOCUMENTS

| | | |
|---|---|---|
| 0241602 | 12/1986 | European Pat. Off. . |
| 2410323 | 9/1975 | Fed. Rep. of Germany . |
| 3602860 | 5/1987 | Fed. Rep. of Germany . |
| 241662 | 6/1946 | Switzerland . |

Primary Examiner—Thomas Wyse
Attorney, Agent, or Firm—Sughrue, Mion, Zinn, Macpeak & Seas

[57] ABSTRACT

The urban waste is crushed (2) to dimensions no greater than 5 cm and intimately mixed (5) with a aqueous suspension of biological sludge preconditioned at a temperature of from 40 to 100° C. (6) and having a dry content of from 3 to 30% by weight, the suspension thus obtained, inoculated with bacterial strains (7) which can effect anaerobic break-down, being supplied to a closed fermentation cell (11, 12, 13) operated as a fluidised bed and being kept under anaerobic fermentation conditions in the cell until the emission of biogas has effectively ceased. In the fermentation cell the suspension percolates through filtration means constituted by a non-woven textile covering the walls and the base of the cell and the flow of percolated suspension is recycled to the cell. The filtration means also facilitate the separation of the biogas evolved.

7 Claims, 2 Drawing Sheets

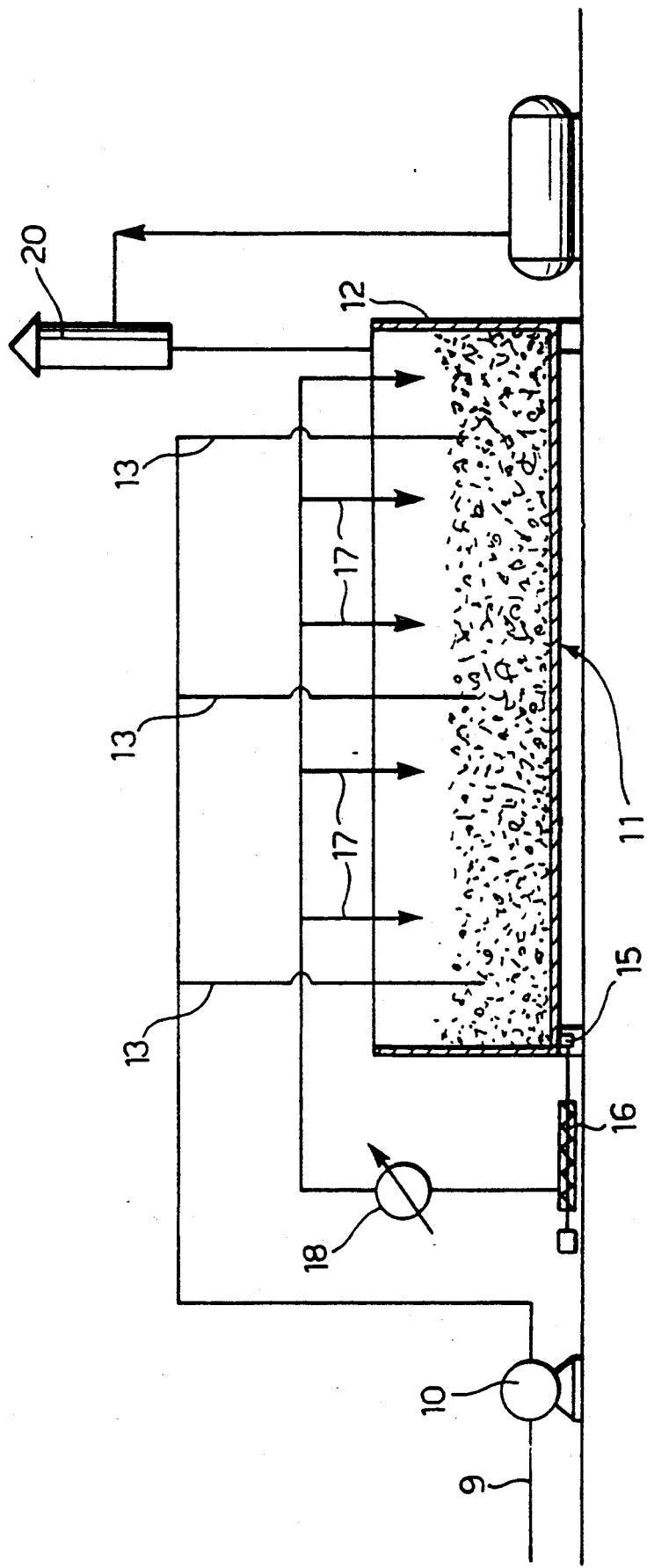

METHOD FOR THE BREAKDOWN AND RECYCLING OF SOLID URBAN WASTE BY ANAEROBIC FERMENTATION

DESCRIPTION

The present invention relates to a method for the break-down and recycling of solid urban waste by means of anaerobic fermentation.

The conventional technique for the break-down of solid urban waste provides for the recovery of re-usable raw materials, such as iron, paper and/or plastics, from the waste by sorting before the rest is left to ferment either spontaneously or after priming with suitable cultures.

In this case the materials recovered are contaminated with putrescible organic substances so that their transport and their working at re-processing plants cause foul-smelling emissions, atmospheric pollution and the risk of dermatosis to the personnel carrying out the re-processing.

In order to avoid these problems, the present invention provides a method characterised in that it comprises the steps of:

a) crushing the solid urban waste, as it is, to dimensions suitable for transport on a fluidised bed, b) mixing the crushed solid urban waste with an aqueous suspension of biological sludge from aerobic purification plants, inoculated with bacterial strains which can effect anaerobic break-down, c) supplying the suspension thus obtained to a fluidised-bed anaerobic fermentation cell, and d) maintaining the suspension under fermentation conditions in the cell until the emission of biogas has effectively ceased.

As a result of the fermentation, the method enables an inert material to be obtained which can be removed from the cell and used as an infill material for land reclamation, or which may be sorted to allow the recovery of raw materials which can be recycled or used as energy sources for the production of electrical energy by means of their gasification.

A further subject of the invention is constituted by the cell for the anaerobic fermentation of the aqueous suspension of urban solids and biological sludge in a fluidised bed, characterised in that it includes a closed containing structure provided with opening means for the discharge of the fermentation product, means for supplying the aqueous suspension to the cell,
means for collecting the biogas produced during the fermentation,
filtration means constituted by a non-woven textile covering the walls and the bottom of the container and adapted to enable the liquid in the suspension to percolate along the walls of the container, and
pumping and supply means for recycling to the cell the liquid which has percolated through the filtration means.

A further subject of the invention is the whole installation for carrying out the method.

Further characteristics and advantages of the present invention will become clear from the detailed description which follows with reference to the appended drawings, provided by way of non-limiting example, in which:

FIG. 1 is a block-schematic diagram illustrating the method of the invention, and FIG. 2 is a schematic view of a fermentation cell for carrying out the method.

With reference to the drawings, solid urban waste 1 is supplied, as it is, without prior sorting, to a grinding mill 2 where it is crushed to dimensions generally between 1 and 5 cm.

From the mill 2, the crushed solid waste is supplied to a mixer 5 constituted, for example, by a screw which mixes it with a flow 4 of an aqueous suspension of biological sludge 3 produced by the aerobic purification of aqueous effluent. The biological sludge used typically has a dry content of between 3 and 30% by weight.

According to a further innovative aspect, before mixing with the solid urban waste, the biological sludge is subjected to a heat-conditioning treatment in an autoclave 6 at a temperature of between 40° and 100° C. for a period of from 10 to 180 minutes and is inoculated with selected bacterial strains 7 in a quantity sufficient to effect the anaerobic break-down of the putrescible material contained in the mixture of solid urban waste and biological sludge.

The solid urban waste and the biological sludge are mixed typically in a ratio of from 10:1 to 10:10 and the mixing process is carried out at a temperature of between 20° and 80° C. over a period of between 1 and 30 minutes.

At the output of the mixer, a flow 8 is added to the mixture in a ratio such as to obtain a flow of a suspension which has a dry content preferably of between 15 and 30% by weight. The suspension 9 is then supplied by a centrifugal pump 10 with a backward rotor to a cell 11a where it undergoes anaerobic fermentation.

The cell 11a which is illustrated in greater detail in FIG. 2, is constituted by a reinforced concrete container provided with a door 12 which can be sealed and is suitable for vehicles for enabling the cell to be emptied of the inert matter at the end of the fermentation process. The suspension 9 is supplied to the cell by means of tubes 13 which extend downwardly into the cell.

The inner surfaces of the base and side walls of the cell 11a are covered with a layer of filtration material 14 constituted by a composite, non-woven textile which has a filtering and draining function such as to retain the solid fraction of the suspension in the cell and enable the liquid phase to percolate along the side walls and the bottom of the cell.

The filtration layer preferably consists 100% of synthetic fibres consolidated mechanically by needling; the fibres have different counts with denier ratios of between 0.1 and 0.3 in dependence on the particle sizes of the solid in the cell itself. By way of non-limiting example, the characteristics of the preferred textile material used in the cell according to the invention are given in the table below.

| Parameter | Unit of measurement | Value |
| --- | --- | --- |
| mass surface density | $g/m^2$ | 1000/1600 |
| nominal thickness | cm | 0.7–1.5 |
| filtration aperture | microns | 65–130 |
| porosity | % | 85 minimum |
| permittivity | $sec^{-1}$ | 1.5–3.0 |
| transmittivity | $m^2/sec$ | $5.10^{-3}$ |
| tensile strength | kN/m | L 20 min. |
|  |  | T 20 min. |
| extension under tension | % | L 100 max. |
|  |  | T 100 max. |

-continued

| Parameter | Unit of measurement | Value |
|---|---|---|
| tear strength | kN/m | L 2 min.<br>T 1.5 min. |

L = longitudinal
T = transverse
min = minimum value
max = maximum value

The cell also has a sump 15 at the bottom in which the aqueous liquid which has percolated through the filtration covering 14 collects, and a recycling duct including a centrifugal pump 16 which takes the percolated liquid from the sump 15 and feeds it into the cell through nozzles 17 situated inside the cell adjacent the ceiling. The recycling duct also includes a heat exchanger 18 which conditions the percolated liquid to the fermentation temperature.

The cell also has manifolds (not illustrated) for collecting the biogas evolved and intended to be recovered or burnt in a burner 20.

Inside the cell a microbiological mechanism is established for the anaerobic conversion of putrescible organic matter containing carbon, hydrogen and oxygen into methane, carbon dioxide and water.

The process is carried out under fluidised bed conditions, with the percolated water being recycled continuously and cooled under static conditions in the water-water heat exchanger 18 to allow for the small amount of heat generated by the process so as to maintain the optimum fermentation temperature and humidity conditions for the metabolism of the bacterial strains selected for the purpose. The fermentation temperature is typically between 30° to 40° C.

By virtue of the permeability of the needled nonwoven textile, the filtered water runs along the walls and the base of the cell, is collected in the sump 15 and, before being recycled to the fluidised bed, is thermostatically adjusted to the preselected temperature.

Still by virtue of the transmittivity of the tufted cloth, the biogases collect at the top of the cell, are taken in by the manifold and are recovered or sent to the burner for destruction.

The rate of the biological conversion can be regulated by means of the metering of the micro-organisms so as to achieve conversion times of between 20 and 60 days.

According to the preferred embodiment, the installation for carrying out the process includes three cells 11a 11b and 11c so as to enable the method to be carried out pseudo-continuously.

Under static operating conditions, at least one cell is operating in the biological conversion phase whilst a second cell is being loaded and the third cell is being emptied.

Towards the end of the biological conversion phase in one cell, the percolated water is cooled gradually and used as the flow 8 for regulating the water content of the suspension output by the mixer 5 as required for supply to the cell which is in the filling phase.

At the same time, the third cell is being emptied. The end of the fermentation reaction is characterised by the cessation of the gaseous emissions. At this point the inert material remaining in the cell is washed with water. The aqueous washing liquid is added to the flow of percolated water, after which the cell is opened.

The damp, inert material, free from putrescible organic substances, is withdrawn by mechanical means and then left to dry in the open air. This material can be used particularly as infill material for land reclamation and may possibly be sorted to enable the recovery of the combustible fraction which can be used to produce electrical energy.

The method according to the invention therefore enables the problems connected with the disposal of solid urban waste and also the problems caused by excess sludge produced by the biological treatment of domestic, and possibly industrial, sewage to be resolved with moderate operation and installation costs. The installation has no impact on the land since it is similar to an industrial installation which can be situated on a limited area without danger to underlying, subterranean water-bearing layers.

We claim:

1. A method for the breakdown and recycling of solid urban waste by means of anaerobic fermentation comprising the steps of:
   (A) mixing a crushed solid urban waste with an aqueous suspension of conditioned biological sludge to produce a waste sludge suspension; and
   (B) subjecting the waste sludge suspension to anaerobic fermentation to produce biogas; wherein
      (i) said conditioned biological sludge comprises biological sludge resulting from aerobic purification of sewage that has been heated to a temperature of from 40° C. to 100° C. for a period of from 10 to 180 minutes, and then inoculating the heated biological sludge with a bacterial strain which can effect anaerobic breakdown of said waste sludge suspension; and
      (ii) said subjecting step is carried out in an anaerobic fermentation cell under fluidized-bed conditions until the biogas production has substantially stopped.

2. A method according to claim 1, wherein the conditioned biological sludge has a dry content of from 3 to 30% and is mixed, in said mixing step, with the solid waste in a ratio of from 10:1 to 10:10.

3. A method according to claim 1, wherein the mixing of the solid urban waste and the conditioned biological sludge is carried out at a temperature of between 20° C. and 80° C. over a period of from 1 to 30 minutes.

4. A method according to claim 1, wherein said mixing step further comprises the adding of a flow of aqueous liquid to the solid urban waste and the biological sludge such that said resulting waste sludge suspension has a dry content of from 15% to 30% by weight.

5. A method according to claim 1, wherein said method further comprises:
   (a) passing a liquid phase of the waste sludge suspension through a filtration covering provided on the walls and bottom of the fermentation cell to obtain a filtered liquid phase;
   (b) cooling the filtered liquid phase; and
   (c) recycling the filtered liquid phase to the fermentation cell.

6. A method according to claim 5, wherein said anaerobic fermentation is carried out in said fermentation cell, said fermentation cell comprising
   a closed container provided with a gas tight opening means for the discharge of the fermentation product,
   supply means for supplying the aqueous suspension to the fermentation cell, collecting means for collecting the biogas produced during the fermentation, a filter comprising a non-woven textile provided on the walls and on the bottom of the container and adapted to enable the liquid in the suspension to percolate along the walls of the container; and pumping and supply means for recycling to the cell the liquid phase which has percolated through the filtration means.

7. A method according to claim 6, wherein the filtration means comprises a non-woven textile having a permeability of from 1.5 to 3 sec$^{-1}$ and filtration pores having a diameter of between 65 and 130 microns.

* * * * *

UNITED STATES PATENT AND TRADEMARK OFFICE
CERTIFICATE OF CORRECTION

PATENT NO. : 5,207,911
DATED : May 4, 1993
INVENTOR(S) : Roberto Pellegrin et al It is certified that error appears in the above-indentified patent and that said Letters Patent is hereby corrected as shown below:

On the title page: Item [30] Foreign Application Priority Data, delete "Mar. 7, 1989" and insert therefor --Mar. 7, 1988--.

Signed and Sealed this

Third Day of May, 1994

Attest:

BRUCE LEHMAN

*Attesting Officer*  *Commissioner of Patents and Trademarks*